United States Patent [19]

Steer et al.

[11] Patent Number: 4,717,388

[45] Date of Patent: Jan. 5, 1988

[54] BAG AND VALVE ASSEMBLY FOR MEDICAL USE

[75] Inventors: Peter L. Steer, Surrey; John V. Edwards, Sussex, both of England

[73] Assignee: E. R. Squibb & Sons, Inc., Princeton, N.J.

[21] Appl. No.: 400,767

[22] Filed: Jul. 22, 1982

[30] Foreign Application Priority Data

Aug. 7, 1981 [GB] United Kingdom ............... 8124291

[51] Int. Cl.⁴ .................................................. A61M 1/00
[52] U.S. Cl. .................................. 604/323; 604/335; 604/408; 604/905
[58] Field of Search ................... 128/DIG. 24, 767; 604/27, 30, 31, 33, 36, 37, 54, 132, 133, 244, 246, 247, 249, 262, 283, 403, 408, 905, 165, 317, 322, 323, 326; 206/828; 215/DIG. 3

[56] References Cited

U.S. PATENT DOCUMENTS

| | | | |
|---|---|---|---|
| 3,298,370 | 1/1967 | Beatty | 128/DIG. 24 |
| 3,312,221 | 4/1967 | Overment | 604/317 |
| 3,460,529 | 8/1969 | Leucci | 128/767 |
| 3,901,235 | 8/1975 | Patel et al. | 128/DIG. 24 |
| 3,967,645 | 7/1976 | Gregory | 604/247 X |
| 4,194,509 | 3/1980 | Pickering et al. | 604/283 X |
| 4,205,690 | 6/1980 | Layton | 604/323 |
| 4,324,242 | 4/1982 | Cross | 604/132 X |
| 4,334,551 | 6/1982 | Pfister | 604/905 X |
| 4,362,156 | 12/1982 | Feller, Jr. et al. | 604/165 |

FOREIGN PATENT DOCUMENTS

| | | | |
|---|---|---|---|
| 2019219 | 10/1979 | United Kingdom | 604/283 |
| 2067075 | 7/1981 | United Kingdom | 604/905 |

Primary Examiner—C. Fred Rosenbaum
Assistant Examiner—H. Macey
Attorney, Agent, or Firm—Lawrence S. Levinson; Stephen B. Davis

[57] ABSTRACT

A bag having a flap valve beneath an opening at the top edge and a second valve including a longitudinally slidable valve member having a downwardly extending tube. When the slidable valve is in the open position the downwardly extending tube passes through the flap valve to provide sterile access to the liquid within the bag.

3 Claims, 2 Drawing Figures

U.S. Patent    Jan. 5, 1988    4,717,388
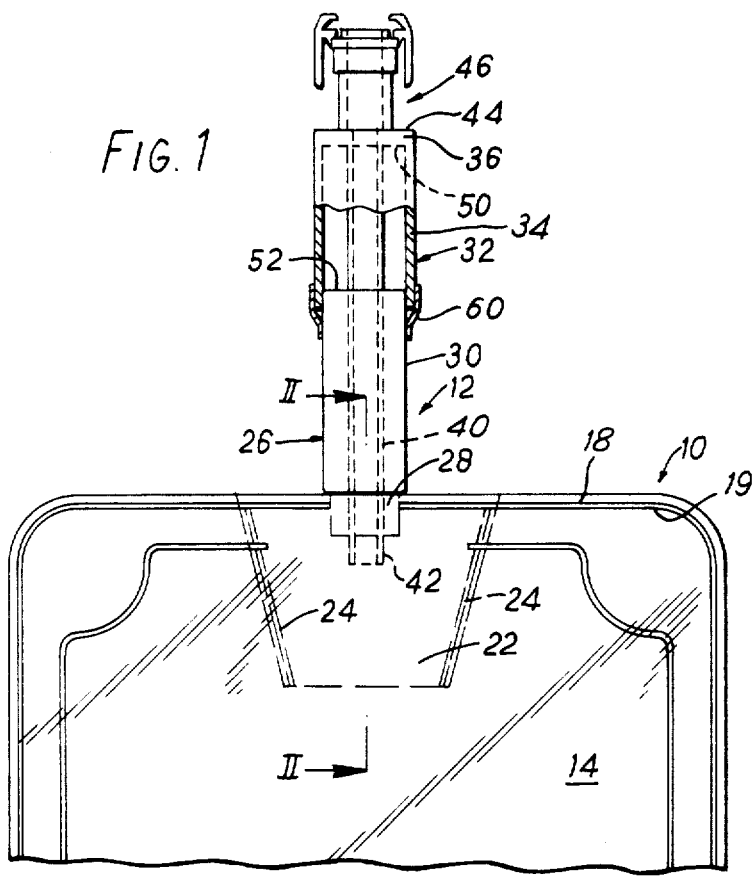
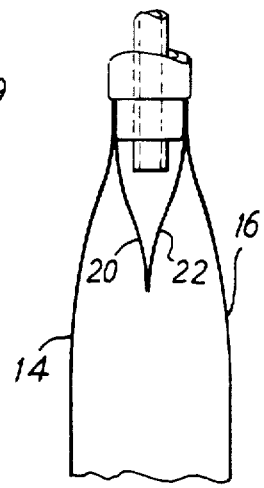

BAG AND VALVE ASSEMBLY FOR MEDICAL USE

BACKGROUND OF THE INVENTION

At the present time in hospitals or day clinics, bladder irrigation, assuming a Foley catheter is in place, is carried out by using a syringe to feed in about 50 cc. of suitable liquid (usually water). This liquid eventually drains out by the same route and is collected in a container. Such irrigation may be done for medical purposes or to clear the tube and the distal outlet of the catheter of any accumulation of substances such as mucus which may block the catheter. The procedure is time-consuming and messy and gives rise to a considerable risk of cross-infection.

Efforts have been made to minimize the cross infection problem by providing special and complicated designs of catheter venting and urine sample collecting units. One example is the arrangement shown by Eisenberg et al. in U.S. Pat. No. 4,116,227.

It would be useful to have available a bag of sterile liquid with the bag parts also entirely sterile. One possibility would be to fill the bag with a non-sterile fluid and then autoclave the bag and its contents. This procedure is unlikely to be attractive economically and has problems as the bags may burst. Another possibility is to use sterile filling procedures of the kind that are well-known to pharmaceutical manufacturers of hospital equipment. In this case, one must ensure that no infection can be introduced when access is gained to the contents of the bag at the time of their use. In other words, the bung, cork, screwcap or other filling must present to the catheter which is fitted to it a totally sterile entrance, otherwise the whole point of sterilizing the bag contents is lost.

OBJECTS OF THE INVENTION

According to the present invention, a bag and valve assembly for medical use are provided including a valve having first and second valve members which can occupy two relative positions namely a valve open and a valve closed position. Initially, the valve members are held in their closed relative position by a manually breakable seal.

According to an advantageous feature of the invention, one of the valve members is tubular and in moving to its open position can be slid between the flaps of a flap valve located within the bag, so allowing access to the bag contents. In a particularly preferred construction according to the invention, said one tubular valve member is arranged to be slidable within an outer tube permanently connected to the bag, and a manually breakable seal is fixed to the exterior of both tubes. The seal may be formed by a thin web or membrane of synthetic plastics material integral with or fixed to the tubular valve member and the outer tube.

BRIEF DESCRIPTION OF THE DRAWINGS

FIG. 1 is a front view of a bag and valve assembly according to the invention;

FIG. 2 is a cross-section on the line II—II in FIG. 1 illustrating the flap valve in the bag and an end of the tube whereby the flap valve may be opened when desired.

DETAILED DESCRIPTION OF THE INVENTION

This invention relates to a bag and valve assembly for medical use, and is particularly although not exclusively intended to provide a convenient means of allowing irrigation via a catheter with a sterile liquid. One example where the invention may be useful is in bladder irrigation.

The illustrated bag and valve assembly for medical use comprises a bag 10 and a valve assembly 12. The bag 10 is basically a conventional bag of the kind used for urine drainage and formed of two superposed plastics sheets 14 and 16. These are welded together by weld seams 18 and 19, as is conventional. A conventional flap valve is included formed by flaps 20, 22 individually welded at their upper ends to the sheets 14 and 16, respectively, and welded to each other by flap valve weld seams 24. The flaps 20, 22 are not connected together at their lower ends and in use they serve as a conventional non-return valve preventing any liquid within the bag 10 from contacting parts of the valve assembly.

A tube 26, for example of synthetic plastics material, is welded or adhesively secured into the top edge of the bag between the superposed sheets 14, 16. This tube has a tube portion 28 of reduced diameter and a cylindrical tube portion 30 extending upwardly outside the bag 10. A tubular valve member 32 is arranged to be longitudinally slidable relative to the tube 26, and the valve member 32 has an external sleeve 34 which slides on the cylindrical portion 30. This sleeve 34 is integral with a body portion 36 and with a downwardly-extending tube 40 whose lower end seen at 42 is located between the flaps 20, 22. Fitted into the upper end 44 of the valve member 32 is a female coupling element 46. Female coupling element 46 is adapted to engage a male coupling on the end of a catheter extending from the patient's body. Preferably, the female and corresponding male coupling elements are of the construction shown in our copending application U.S. Ser. No. 336,479 filed Dec. 31, 1981, now abandoned in favor of continuation application Ser. No. 599,132, filed Apr. 11, 1984. Female coupling element 46 may be secured to the valve member 32 by adhesive or by a force fit or in any other convenient way that will provide a closed and sealed connection.

The operation of the valve assembly will readily be understood. When the valve member 32 is in position, relative to the tube 26, as illustrated in FIG. 1, then no liquid can escape from the bag because the flaps 20, 22 of the flap valve remain in contact, said valve being thereby closed. When it is desired to expel or draw off liquid from the interior of the bag 10, the valve member 32 is moved axially downwardly relative to the tube 26 to its full extent, that is to say until the surface 50 on the body portion 36 comes into engagement with the upper end 52 of the cylindrical tube portion 30, so limiting the movement. This movement causes the lower end 42 of the down tube 40 to pass between the lower edges of the flaps 20, 22 and consequently any liquid in the bag may then proceed straight into the tube 40 and through it to the interior of the female coupling element 46. If desired this may be achieved by gently squeezing the bag 10, once the valve member 32 has been brought into its open position.

A manually breakable seal 60, for example of synthetic plastics material, surrounds and is integral with or secured to both the cylindrical tube portion 30 and the valve element 32. The seal 60 may for example consist of a thin web or memberane of plastics material which can easily be ruptured by relative rotation of the sleeve 32 and the tube 26. Other manually breakable seals between these two parts may of course be employed without departing from the present invention.

In one manner of employing the invention disclosed herein, the bag and valve assembly is manufactured and is irradiated to make it sterile in a conventional manner in the valve-opened position with the breakable seal 60 unbroken. At this time of course the bag is empty. The bag is then filled by a sterile filling proceudre, connecting a suitable nozzle to the female coupling element 46. A suitable nozzle may include a male coupling element as disclosed and illustrated in U.S. Ser. No. 336,479 referred to above. Such a male coupling element is then removed and a male coupling element in the form of a stopper is engaged with the female coupling element 46, all under sterile conditions. One then has a bag and valve assembly, completely sterile, and filled with the desired liquid. At this time the contents of the bag cannot be squeezed out because of the non-return action of the flap valve 20, 22. The valve member 32 cannot be moved relative to the tube 26 because of the seal 60.

When the bag is required to be used in a hospital or a clinic, a Foley catheter is used provided with a male coupling element as disclosed in U.S. Serial No. 336,479. As an alternative, any other readily releasable and connectible connector could be used and in such an event one coupling element thereof would be included in place of the coupling element 46. The nurse at the hospital or clinic removes the male stopper coupling element and connects the element 46 to its male counterpart on the Foley catheter. The nurse then twists the valve element 32 relative to the tube 26 to break the seal 60 and then moves the valve element 32 axially downward relative to the tube 26 to push the end 42 between the lower edges of the flaps 20, 22. In this condition of the parts, the contents of the bag 10 can be gently squeezed directly into the patient's bladder without any possibility of non-sterile surfaces or materials being able to enter the bladder.

After the requisite time has elapsed, the patient's bladder will squeeze the irrigation fluid back directly into the then empty bag 10. When this is completed, the valve member32 is moved axially away from the bag 10 to withdraw the tube end 42 to the position illustrated in FIG. 1. The two flaps of the flap valve then prevent any escape of material from the interior of the bag 10. The bag 10 can then be immediately disposed of. It will be seen that the procedure described is a simple trouble free quick procedure maintaining entirely sterile conditions and is a great advance on the time consuming manipulations previously necessary to carry out the same task.

The invention can be applied otherwise than in bladder irrigation. For example, such a bag and valve assembly could be useful in peritoneal dialysis and a drainage bag and valve assembly of this kind, could be worn by the patient while draining is taking place.

What is claimed is:

1. A bag and valve assembly for medical use, said bag comprising two sheets of plastics material welded together around their periphery except for an opening at the top edge, a flap valve comprising two flaps of plastics material individually welded at their upper edges to the sheets of plastics material which form said bag so that said top edge opening leads into said flap valve, said flaps also welded to each other along their side edges but not connected at their lower edges, and a second valve comprising a first tubular member secured to said top bag opening and a second longitudinally slidable tubular valve member having a downwardly extending tube which in the open position passes down through said first tubular member and extends between said flaps so as to provide access to the contents of said bag, said first tubular member having a cylindrical portion extending upwardly outside said bag and said longitudinally slidable tubular valve member having an external sleeve which slides on said cylindrical portion so as to move said downwardly extending tube from a closed to an open position.

2. A bag and valve assembly as in claim 1 wherein said cylindrical portion of said first tubular member and said external sleeve of said longitudinally slidable valve member are affixed by a manually breakable seal.

3. A bag and valve assembly as in claim 1 wherein a female coupling element is affixed to the upper end of said longitudinally slidable valve member.

* * * * *

UNITED STATES PATENT AND TRADEMARK OFFICE
CERTIFICATE OF CORRECTION

PATENT NO. : 4,717,388
DATED : January 5, 1988
INVENTOR(S) : Peter L. Steer & John V. Edwards It is certified that error appears in the above-identified patent and that said Letters Patent is hereby corrected as shown below:

On the title page

"[73] Assignee: E. R. Squibb & Sons, Inc., Princeton, N.J."

should read

-- [73] Assignee: Craig Medical Products Limited, Sussex, England --

Signed and Sealed this

Twenty-first Day of June, 1988

Attest:

*Attesting Officer*

DONALD J. QUIGG

*Commissioner of Patents and Trademarks*